(12) United States Patent
Gericke

(10) Patent No.: US 7,953,202 B2
(45) Date of Patent: May 31, 2011

(54) MEDICAL IMAGING METHOD AND SYSTEM WITH AUTOMATED ASSOCIATION OF IMAGES WITH MEASUREMENT SEQUENCES

(75) Inventor: Ralph Gericke, Gerhardshofen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/423,102

(22) Filed: Apr. 14, 2009

(65) Prior Publication Data

US 2009/0256566 A1 Oct. 15, 2009

(30) Foreign Application Priority Data

Apr. 14, 2008 (DE) .......................... 10 2008 018 725

(51) Int. Cl.
*A61B 6/00* (2006.01)
(52) U.S. Cl. .......................................... 378/4; 378/210
(58) Field of Classification Search ...... 378/4; 382/131, 382/132
See application file for complete search history.

(56) References Cited

U.S. PATENT DOCUMENTS

| | | | | |
|---|---|---|---|---|
| 5,041,789 A | * | 8/1991 | Keller et al. | 324/318 |
| 6,125,209 A | * | 9/2000 | Dorricott | 382/233 |
| 6,661,228 B2 | | 12/2003 | Haworth et al. | |
| 6,891,920 B1 | | 5/2005 | Minyard et al. | |
| 2002/0057850 A1 | * | 5/2002 | Sirohey et al. | 382/299 |
| 2002/0065460 A1 | * | 5/2002 | Murao | 600/425 |
| 2003/0002631 A1 | * | 1/2003 | Gaddipati et al. | 378/210 |
| 2003/0123603 A1 | * | 7/2003 | Suzuki | 378/4 |
| 2004/0161139 A1 | * | 8/2004 | Samara et al. | 382/131 |
| 2005/0063575 A1 | * | 3/2005 | Ma et al. | 382/128 |

\* cited by examiner

*Primary Examiner* — Edward J Glick
*Assistant Examiner* — Alexander H Taningco
(74) *Attorney, Agent, or Firm* — Schiff Hardin LLP

(57) ABSTRACT

A medical imaging system is operated corresponding to a measurement sequence to acquire data of an examination subject. A control device associates a reference to the measurement sequence with the acquired data and stores the acquired data including the associated reference. The control device determines an image of the examination subject using the acquired data and outputs the determined image to an operator of the medical imaging system via a viewing device. When a corresponding activation command is provided to it by the operator, the control device automatically determines the corresponding measurement sequence using the reference associated with the displayed image, and automatically associates a reference to at least one image corresponding with the displayed image with the measurement sequence. The control device provides the measurement sequence (S) for search purposes upon retrieval of the measurement sequence, the control device also automatically retrieves the images associated with the retrieved measurement sequence as well.

11 Claims, 4 Drawing Sheets

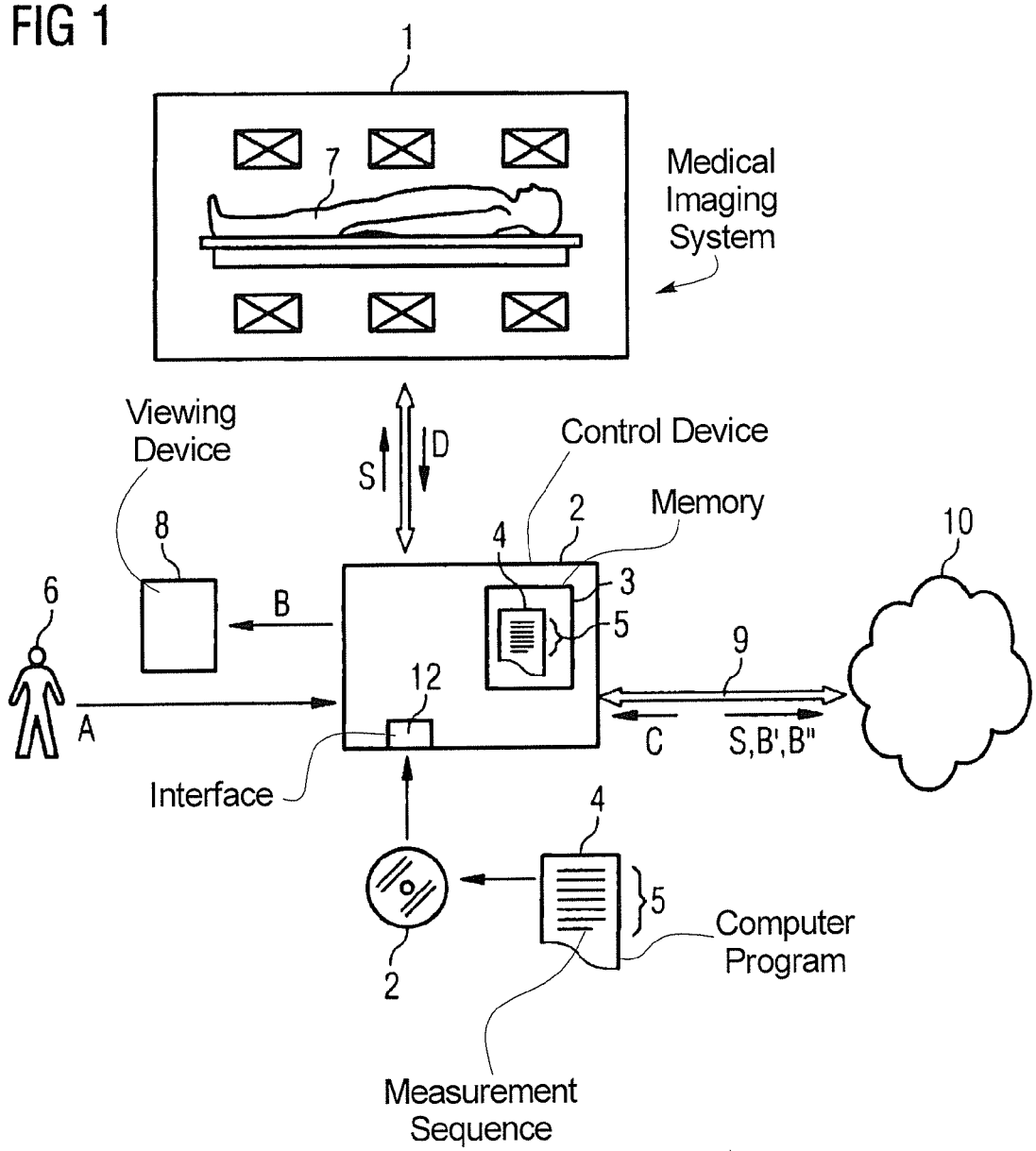

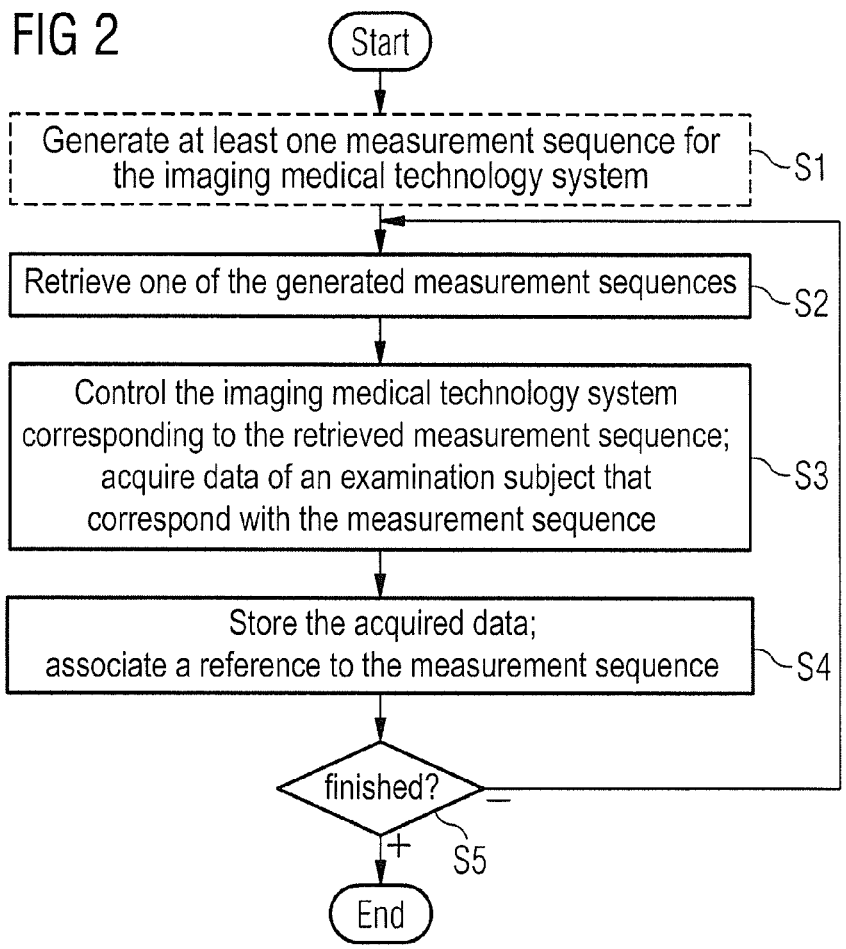
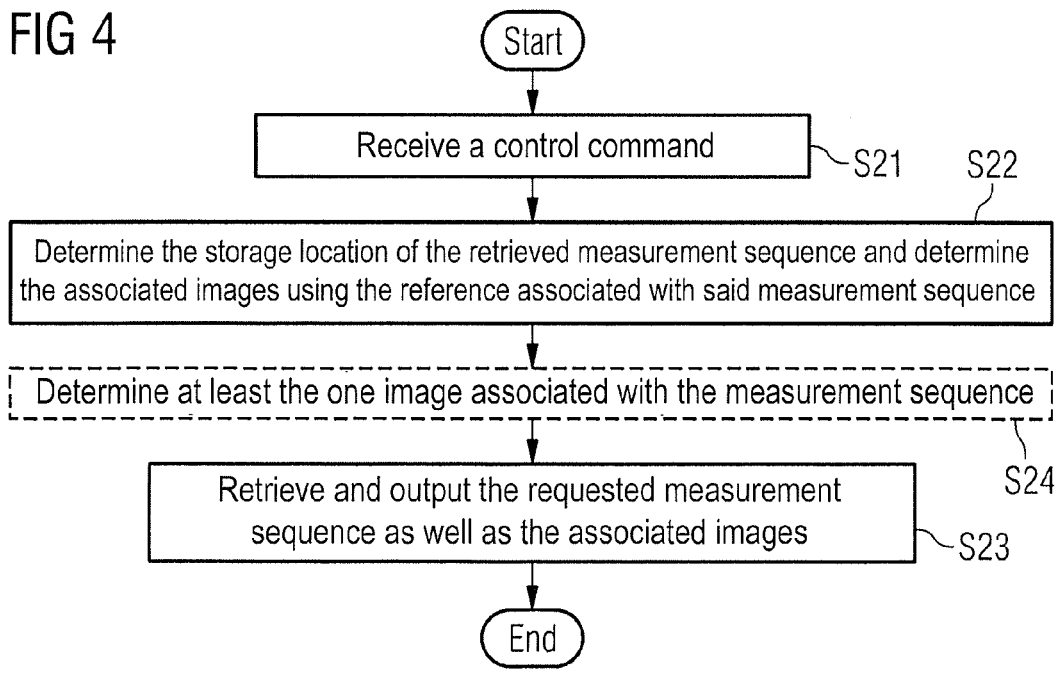

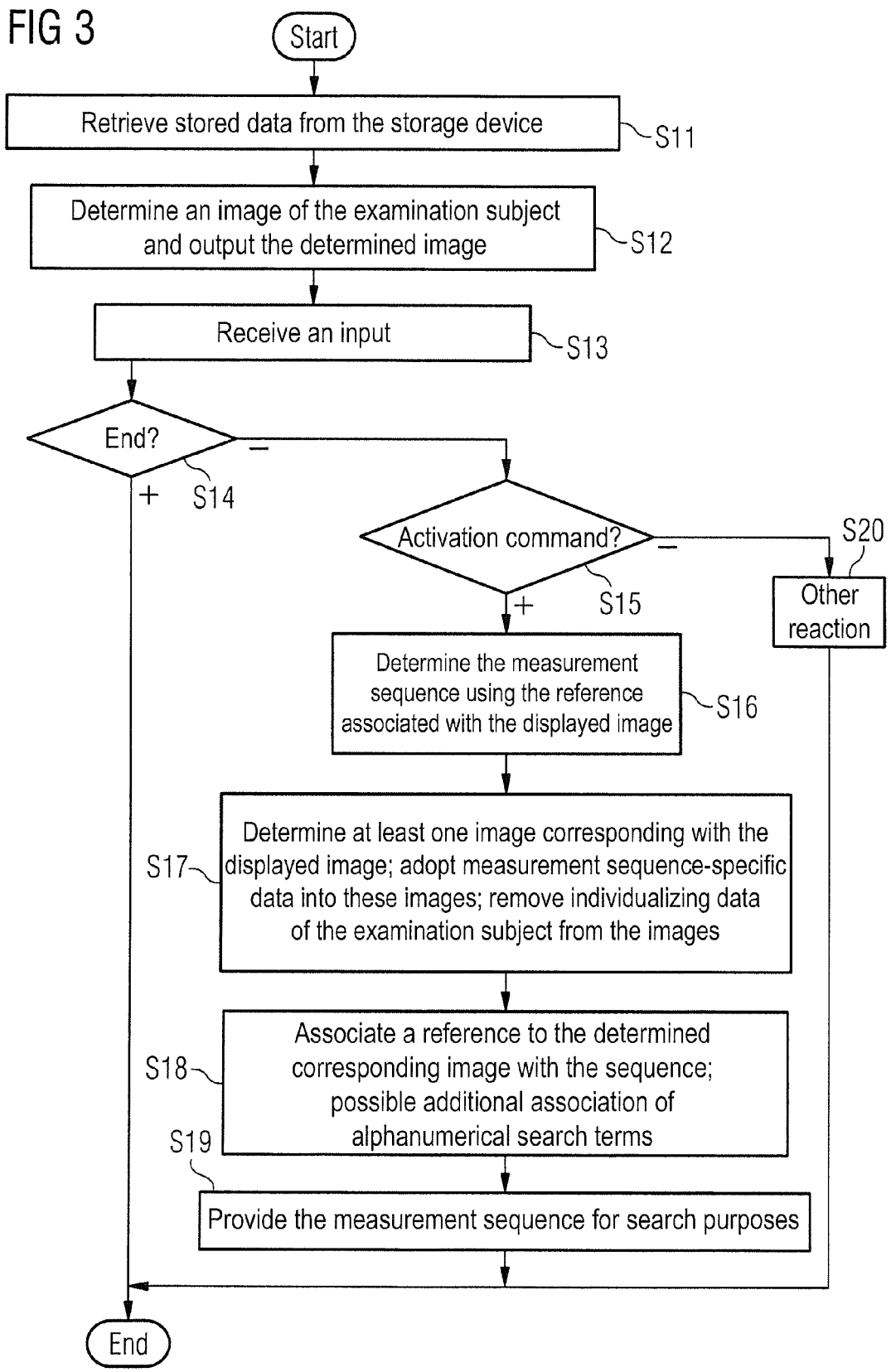

MEDICAL IMAGING METHOD AND SYSTEM WITH AUTOMATED ASSOCIATION OF IMAGES WITH MEASUREMENT SEQUENCES

BACKGROUND OF THE INVENTION

1. Field of the Invention

The present invention concerns an operating method for a control device for a medical imaging system of the type wherein the control device controls the medical imaging system corresponding to a measurement (data acquisition) sequence to acquire data from an examination subject, and wherein the control device determines an image of the examination subject using the acquired data and outputs the determined image to an operator of the imaging medical technology system via a viewing device.

The present invention also concerns a computer-readable medium encoded with programming instructions to implement a method of the type described above.

Furthermore, the present invention concerns a control device on which such a computer-readable medium is stored such that it can be executed by the control device. Finally, the present invention concerns a medical imaging system that embodies such a control device.

2. Description of the Prior Art

Methods and systems of the above general type are known, for example, from U.S. Pat. No. 6,661,228.

In medical imaging, simple operating functionalities are increasingly gaining in importance. One example of such an operating functionality is the selection of a desired measurement sequence for a specific medical question.

Measurement sequences—thus the sequence of the individual control commands of a measurement procedure—are for the most part developed by application specialists (also by users in individual cases). Using the measurement sequences themselves, the normal user cannot easily recognize which functionalities and possibilities a particular measurement sequence offers. The medical technology system therefore must provide not only the measurement sequences as such to the normal user. Rather, expanded information must also be provided to the normal user using which said normal user can recognize the reason, purpose, effect and possibilities of the respective measurement sequence.

In principle the expanded information can be provided to the user in arbitrary form, for example as text or as an image. Both types of information can hereby in principle be provided both in printed and in electronic form.

SUMMARY OF THE INVENTION

An object of the present invention is to allow expanded information in the form of at least one electronic image to be associated with the corresponding measurement sequence in a simple manner.

The above object is achieved according to the invention by an operating method of the aforementioned type wherein the control device associates a reference (link, pointer) to the measurement sequence with the acquired data, and stores the acquired data including the associated reference, the control device, when a corresponding activation command is provided to it by the operator, automatically determines the corresponding measurement sequence using the reference associated with the displayed image, and automatically associates a reference to at least one image corresponding with the displayed image with the measurement sequence, the control device provides the measurement sequence for search purposes and, upon a retrieval of the measurement sequence, the control device also automatically retrieves the images associated with the retrieved measurement sequence.

The displayed image may include individualizing data for the examination subject. If so, in an embodiment of the method, in the generation of the images associated with the retrieved measurement sequence, the control device removes the individualizing data of the examination subject from the images associated with the retrieved measurement sequence.

It is also possible that the displayed image includes measurement sequence-specific data. In this case it is advantageously provided for the control device to adopt the measurement sequence-specific data into the images associated with the retrieved measurement sequence given the generation of the images associated with the retrieved measurement sequence.

One of the images associated with the retrieved measurement sequence may be unscaled relative to the displayed image. If so, in the generation of the images associated with the retrieved measurement sequence, the control device can scale at least one of the images associated with the retrieved measurement sequence relative to the displayed image.

In the event that more than one image is associated with the measurement sequence, both procedures are also possible in combination.

Furthermore, the control device can associate a reference to an additional image associated with the retrieved measurement sequence with the scaled image. The additional image in this case has a higher resolution than the scaled image.

The control device can generate at least one of the images associated with the retrieved measurement sequence only upon retrieval of the measurement sequence. It is likewise possible for the control device to already generate at least one of the images associated with the retrieved measurement sequence based on the requirements of the activation command.

The above object also is achieved in accordance with the present invention by a computer-readable medium encoded with programming instructions that, when loaded into a control device of a medical imaging system, cause the control device and the medical imaging system to implement a method as described above, including all embodiments.

The above object also is achieved in accordance with the invention by a control device on which is stored a computer program according to the invention that can be executed by the control device.

The above object also is achieved in accordance with the invention by a medical system that has a control device fashioned according to the invention. The medical imaging system can be fashioned as a magnetic resonance system.

BRIEF DESCRIPTION OF THE DRAWINGS

FIG. 1 schematically illustrates a medical imaging system constructed and operating in accordance with the present invention.

FIGS. 2 through 4 are flow charts describing embodiments of the method in accordance with the present invention.

DESCRIPTION OF THE PREFERRED EMBODIMENTS

Figure 5:
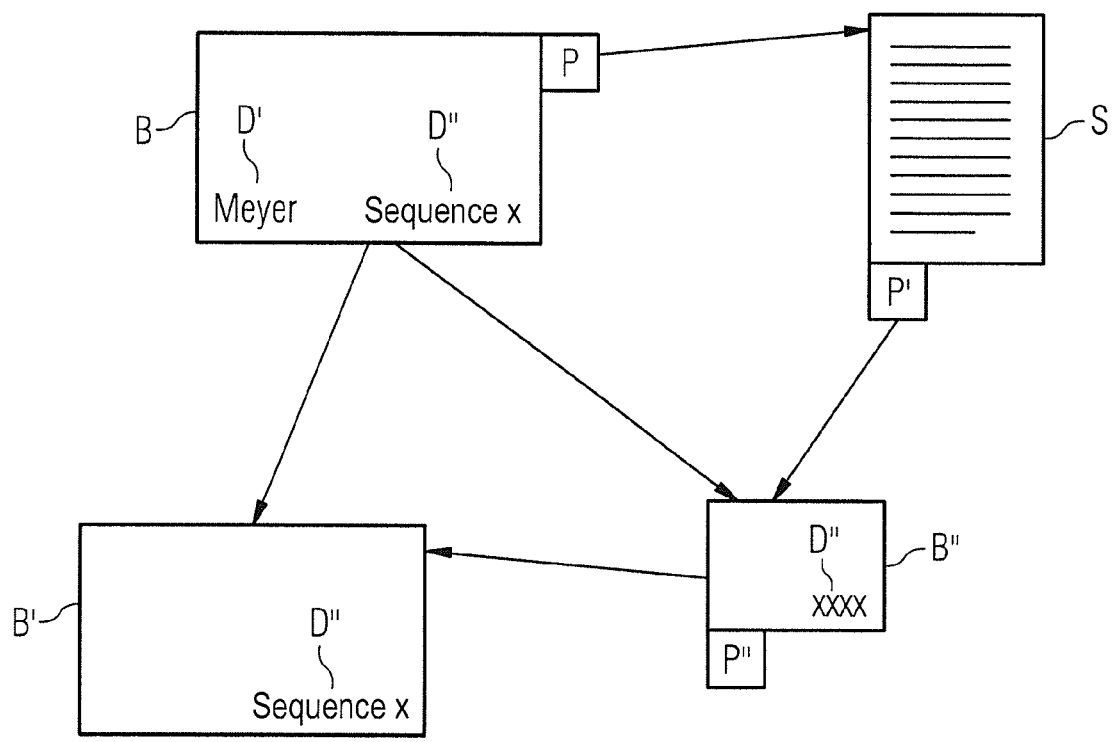
FIG. 5 schematically illustrates various images obtained in accordance with the inventive method.

According to FIG. 1, an medical imaging system 1 is fashioned as a magnetic resonance system. However, the design as a magnetic resonance system is purely exemplary. Alternatively, for example, the imaging medical technology system 1 could be fashioned as an x-ray system (C-arm system or computed tomography) or as an ultrasound tomography apparatus.

The imaging medical technology system 1 has a control device 2 by means of which the medical imaging system 1 is controlled. The control device 2 is fashioned as a software-programmable control device 2. A computer program 4 is therefore stored in a memory device 3 of the control device 2, which computer program 4 is executed by the control device 2 in operation. The computer program 4 embodies machine code 5 that can be directly executed by the control device 2. The execution of the machine code 5 by the control device 2 has the effect that the control device 2 is operated according to an operating method that is explained in detail in the following.

According to FIG. 2, at least one measurement sequence S for the imaging medical technology system 1 is created in Step S1. Step S1 is optional and is drawn only with dashed lines in FIG. 2 for this reason. Alternatively, the measurement sequences S could already have been created.

In Step S2, an operator 6 of the imaging medical technology system 1 retrieves one of the generated measurement sequences S. The retrieval of the corresponding measurement sequence S has the effect that, in Step S3, the control device 2 controls the medical imaging system 1 corresponding to the measurement sequence S and acquires data D of an examination subject 7 corresponding with the measurement sequence S.

In Step S4, the control device 2 stores the acquired data D. It hereby associates a reference P to the measurement sequence S with the acquired data D. It thus stores the acquired data D including the associated reference P. The reference P can, for example, be a pointer.

In Step S5, the control device 2 checks whether an additional measurement sequence S should be executed, or whether the acquisition of data D should be ended. Depending on the result of the check of Step S5, the control device 2 returns to Step S2 or ends the execution of measurement sequences S.

In the preceding the data acquisition was explained in connection with FIG. 2. In the following the evaluation of the acquired data D is explained in connection with FIG. 3. The evaluation of the acquired data D can immediately follow the acquisition of the data D so that the acquisition and evaluation of the data D are to be viewed as a unit. Alternatively, however, the evaluation of the data D can ensue separately at a later point in time.

According to FIG. 3, in Step S11 the control device 2 retrieves stored data D from the memory device 3 (naturally due to a corresponding input by the operator 6). Using the retrieved data D the control device 2 determines in Step S12 an image B of the examination subject 7 and outputs the determined image B to the operator 6 via a viewing device 8. It then receives an input from the operator 6 in Step S13.

In Step S14, the control device 2 checks whether the input of Step S13 is a command to end the output of images B. Depending on the result of the check of Step S14, either the procedure from FIG. 3 is abandoned or it transitions to Step S15.

In Step S15, the control device 2 checks whether the input of Step S13 is an activation command A. If this is the case, the control device 2 executes subsequent Steps S16 through S19. Otherwise, it transitions to Step S20.

In Step S16, the control device 2 automatically determines the corresponding measurement sequence S using the reference P associated with the displayed image B. In Step S17 the control device 2 then determines—using the displayed image B—at least one image B', B" corresponding with the displayed image B. Furthermore, in Step S18 it automatically associates the measurement sequence S determined in Step S16 with a reference P' to the corresponding images B'. B" determined in Step S17. The reference P' can be a pointer P', analogous to the reference P. Alphanumerical search terms can additionally be reasonably associated with the measurement sequence S. The search terms are also stored as necessary.

In Step S19 the control device 2 provides the measurement sequence S for search purposes, possibly including the alphanumerical search terms. For example, the control device 2 can cause the corresponding measurement sequence S to be externally searchable by means of the search terms by the operator 6 of the medical imaging system 1, or from outside the control device 2 via a connection 9 to a computer network 10 (for example the Internet).

In Step S20, the control device 2 implements a different reaction. The other reaction can hereby be of an arbitrary nature in principle. In particular, it can depend on the input of Step S13. The reaction of Step S20 can in particular be the retrieval of data D corresponding to Step 11 in addition to the subsequent determination of an image B and its presentation via the viewing device 8 according to Step S12. However, other reactions are likewise possible.

If the measurement sequence S should be retrieved, according to FIG. 4 the control device 2 initially receives a corresponding retrieval command C. The measurement sequence S to be retrieved can hereby have been determined using the search terms associated with the measurement sequence S. In Step S22, the control device 2 determines the storage location of the measurement sequence S to be retrieved and the associated images B', B" using the reference P' associated with the measurement sequence S. In Step S23, the control device 2 then automatically retrieves the requested measurement sequence S as well as the associated images B', B" and outputs them. For example, the output to the operator 6 can ensue via the viewing device 8. However, the output can likewise ensue via the connection 9 to the computer network 10.

As is shown in FIG. 5, individualizing data D' of the examination subject 7 can be associated with the image B that was determined using the acquired data D. Measurement sequence-specific data D" can likewise be associated with the image B. According to FIG. 5, the associated images B', B" do in fact contain the measurement sequence-specific data D", not the individualizing data D' of the examination subject 7. In the scope of the determination of the corresponding images B', B" (see Step S17 from FIG. 3), the control device 2 thus accepts the measurement sequence-specific data D" into the images B', B" in the generation of said images B', B". By contrast, according to Step S17, in the generation of the images B', B" the control device 7 removes the individualizing data D' of the examination subject 7 from said images B', B".

In the scope of the present invention, it is in principle sufficient to associate a single image B', B" with the measurement sequence S. It is alternatively possible that the image B', B" associated with the measurement sequence S is unscaled or scaled relative to the displayed image B. According to FIG. 5, for example, the image B' is unscaled relative to the displayed image B, meaning that it has the same resolution. By contrast, according to FIG. 5 the image B" is scaled relative to the displayed image B, meaning that it has a reduced resolution.

If multiple images B', B" are associated with the measurement sequence S, the associated images B', B" are normally scaled differently. In this case, a reference P'" to the image B' with the better resolution can in particular be associated with the image B" with the poorer resolution. The association of the reference P'" is conducted by the control device 2. The image B' to which the reference P'" refers can itself already be scaled relative to the displayed image B. However, in this case the scaling is less than the scaling of the image B". Alternatively, the image B' with the better resolution can be unscaled relative to the displayed image B. The reference P'" can be a pointer, analogous to the references P, P'.

The presence of the reference P'" in particular enables only the image B" to be initially displayed upon retrieval of the measurement sequence S, and the image B' to be displayed only after a corresponding input by the retriever. The corresponding procedure is generally known under the term "thumbnail".

It is possible (see Step S17 from FIG. 3) that the control device 2 already generates one, multiple or all of the images B', B" based on the specification of the activation command A. Alternatively, it is possible that the control device 2 only generates one, more or all of the images B', B" upon retrieval of the measurement sequence S, corresponding to Step S24 (drawn with dashed lines in FIG. 4). Hybrids of these procedures are also possible. For example, the control device 2 can generate the image B' in the framework of Step S17, the image B" in the framework of Step S24. The reverse procedure is also possible.

The programming of the control device 2 can occur arbitrarily (as desired). For example, the control device 2 can already have been programmed with the computer program 4 before the delivery to the operator 6. Alternatively, it is possible to supply the computer program 4 of the control device 2 via the computer network 10 and the connection 9 to the computer network 10. Alternatively, it is possible to store the computer program 4 on a data medium 11 in an exclusively machine-readable form and to read out the data medium 11 via a suitable interface 12 of the control device 2. The data medium 11 in FIG. 1 is shown (as an example) as a CD-ROM. Alternatively, for example, the data medium 11 could be fashioned as a USB memory stick or as a memory card.

The present invention has many advantages. In particular, it can be realized in a simple manner. Furthermore, via the procedure according to the invention it is ensured that the images B', B" associated with the measurement sequence S actually reflect measurement results that were determined under the control of the imaging medical technology system 1 with precisely this measurement sequence S.

Although modifications and changes may be suggested by those skilled in the art, it is the intention of the inventor to embody within the patent warranted hereon all changes and modifications as reasonably and properly come within the scope of his contribution to the art.

I claim as my invention:

1. An operating method for a medical imaging system, comprising the steps of:

through a computerized control device, acquiring medical image data by controlling operation of a medical imaging system according to a measurement sequence entered into the control device, that defines said operation of the medical imaging system to acquire said medical imaging data from an examination subject interacting with the medical imaging system, by implementing the measurement sequence;

in said control device, automatically associating a reference to the measurement sequence with the acquired data, and storing the acquired data together with the associated reference;

in said control device, automatically reconstructing an image of the examination subject using the acquired data and emitting the image as an output for display at a viewing device of the medical imaging system;

manually entering an activation command into the control device and thereby causing the control device to automatically identify said measurement sequence using the reference associated with the acquired data from which the image was reconstructed, and to automatically associate a further reference to the measurement sequence with at least one image corresponding with the displayed image;

in said control device, making said measurement sequence available for searching; and in said control device, upon retrieval of the measurement sequence in a search, automatically also retrieving all images associated, through said further reference, with the retrieved measurement sequence.

2. A method as claimed in claim 1 comprising including, in said display image, individualizing data of the examination subject and, in said control device, generating the images associated with the retrieved measurement sequence, by removing said individualizing data therefrom.

3. A method as claimed in claim 1 comprising including measurement sequence-specific data in said displayed image and, in said control device, incorporating said measurement sequence-specific data into said images associated with the retrieved measurement sequence upon retrieval thereof.

4. A method as claimed in claim 1 comprising generating one of said images associated with the retrieved measurement sequence as an unscaled image relative to the displayed image.

5. A method as claimed in claim 1 comprising generating said images associated with the retrieved measurement sequence by, in said control device, scaling at least one of said images associated with the retrieved measurement sequence relative to the displayed image.

6. A method as claimed in claim 5 comprising, in said control device, associating a reference to an additional image associated with the retrieved image with the scaled image, and generating said additional image with a higher resolution than said scaled image.

7. A method as claimed in claim 1 comprising, in said control device, generating at least one of said images associated with the retrieved measurement sequence only upon retrieval of said measurement sequence.

8. A method as claimed in claim 1 comprising, generating and storing at least one of said images associated with the retrieved measurement sequence based on requirements of said activation command.

9. A non-transitory computer-readable storage medium encoded with programming instructions that, when loaded into a control device of a medical imaging system, cause the control device and the medical imaging system to:

the medical imaging system according to a measurement sequence, entered into the control device, that defines said operation of the medical imaging system to acquire said medical imaging data from an examination subject interacting with the medical imaging system, by implementing the measurement sequence;

in said control device, automatically associate a reference to the measurement sequence with the acquired data, and store the acquired data together with the associated reference;

in said control device, automatically reconstruct an image of the examination subject using the acquired data and emit the image as an output for display at a viewing device of the medical imaging system;

allow manual entry of an activation command into the control device that causes the control device to automatically identify said measurement sequence using the reference associated with the acquired data from which the image was reconstructed, and to automatically associate a further reference to said measurement sequence with at least one image corresponding with the displayed image;

in said control device, make said measurement sequence available for searching; and in said control device, upon retrieval of the measurement sequence in a search, automatically also retrieve all images associated, through said further reference, with the retrieved measurement sequence.

10. A control device for a medical imaging system programmed to:

acquire medical image data by controlling operation of a medical imaging system according to a measurement sequence entered into the control device, that defines said operation of the medical imaging system to acquire said medical imaging data from an examination subject interacting with the medical imaging system, by implementing the measurement sequence;

automatically associate a reference to the measurement sequence with the acquired data, and store the acquired data together with the associated reference;

automatically generate an image of the examination subject using the acquired data and emit the image as an output for display at a viewing device of the medical imaging system;

allow manual entry of an activation command into the control device that causes the control device to automatically identify said measurement sequence using the reference associated with the acquired data from which the image was reconstructed, and to automatically associate a further reference to the measurement sequence with at least one image corresponding with the displayed image;

make said measurement sequence available for searching; and upon retrieval of the measurement sequence in a search in said control device, automatically also retrieve all images associated, through said further reference, with the retrieved measurement sequence.

11. A medical imaging system for a medical imaging system, comprising:

a data acquisition system controlled by a control device;

said control device being configured to acquired medical image data by controlling operation of the medical imaging system according to a measurement sequence, entered into the control device, that defines said operation of the medical imaging system to acquire said medical imaging data from an examination subject interacting with the medical imaging system, by implementing the measurement sequence;

said control device being configured to automatically associate a reference to the measurement sequence with the acquired data, and to store the acquired data together with the associated reference;

a viewing device;

in said control device being configured to automatically generate an image of the examination subject using the acquired data and to emit the image as an output for display at said viewing device;

an input unit allowing manual entry of an activation command into the control device that causes the control device to automatically identify said measurement sequence using the reference associated with the acquired data from which the image was reconstructed, and to automatically associate a further reference to the measurement sequence with at least one image corresponding with the displayed image;

said control device being configured to make said measurement sequence available for searching; and said control device being configured, upon retrieval of the measurement sequence in a search, to automatically also retrieve all images associated, through said further reference, with the retrieved measurement sequence.

* * * * *